United States Patent [19]

Page et al.

[11] 4,082,086
[45] Apr. 4, 1978

[54] ECG MONITORING PAD

[75] Inventors: Dennis M. Page, Hinsdale; Albert J. Bevilacqua, Downers Grove, both of Ill.

[73] Assignee: M I Systems, Inc., Westmont, Ill.

[21] Appl. No.: 749,796

[22] Filed: Dec. 13, 1976

[51] Int. Cl.² ............................................... A61B 5/04
[52] U.S. Cl. ........................... 128/2.06 E; 128/417; 128/DIG. 4; 29/629; 29/630 R
[58] Field of Search ............. 128/2.06 E, 2.1 E, 404, 128/416, 417, 418, DIG. 4; 29/629, 630 R

[56] References Cited

U.S. PATENT DOCUMENTS

| | | | |
|---|---|---|---|
| 2,943,628 | 7/1960 | Howell | 128/418 |
| 3,323,514 | 6/1967 | Barrett, Jr. | 128/2.06 E |
| 3,387,608 | 6/1968 | Figar | 128/2.06 E |
| 3,409,737 | 11/1968 | Settler et al. | 128/2.06 E |
| 3,476,104 | 11/1969 | Davis | 128/2.06 E |
| 3,805,769 | 4/1974 | Sessions | 128/2.06 E |
| 3,834,373 | 9/1974 | Sato | 128/2.06 E |
| 3,888,240 | 6/1975 | Reinhold, Jr. et al. | 128/2.06 E |

FOREIGN PATENT DOCUMENTS 274,612  7/1951  Switzerland ................... 128/DIG. 4

*Primary Examiner*—Robert W. Michell
*Assistant Examiner*—Lee S. Cohen
*Attorney, Agent, or Firm*—Olson, Trexler, Wolters, Bushnell & Fosse

[57] ABSTRACT

There is disclosed an ECG monitoring device for attachment to the skin of an individual, which device includes a plurality of electrodes for monitoring bio-skin potential disposed at suitable locations on a base or substrate. The device includes a first resilient sponge-like sheet, and a second resilient sponge-like sheet adhesively attached to the first sheet and having a plurality of openings formed therein. A number of electrodes are attached to the second sheet by an adhesive coating, with the connector elements of the respective electrodes in place in the openings and secured to lead wires for attachment to monitoring apparatus. The individual electrodes include an adhesive base surface that can be exposed upon removal of a cover structure which normally overlies a pre-gelled pad and said base surface. The adhesively coated base surfaces of the electrodes are used to affix the device to the patient.

13 Claims, 5 Drawing Figures

U.S. Patent      April 4, 1978      4,082,086
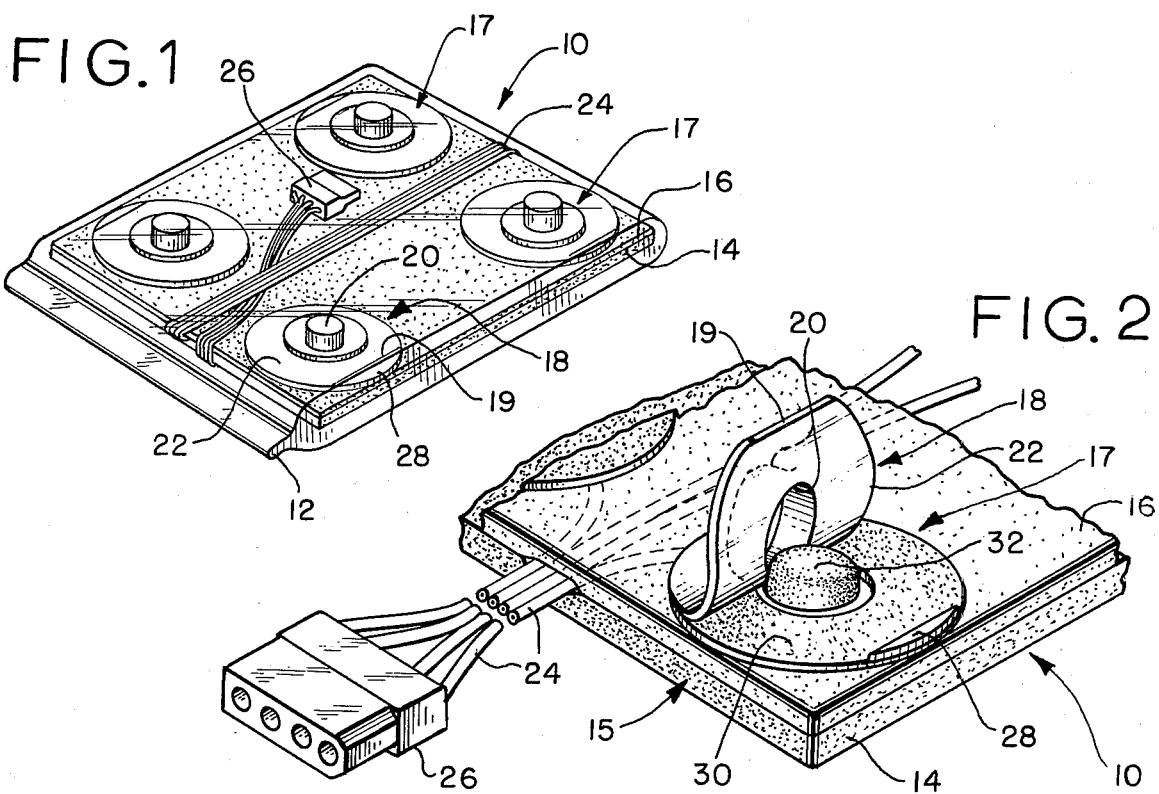
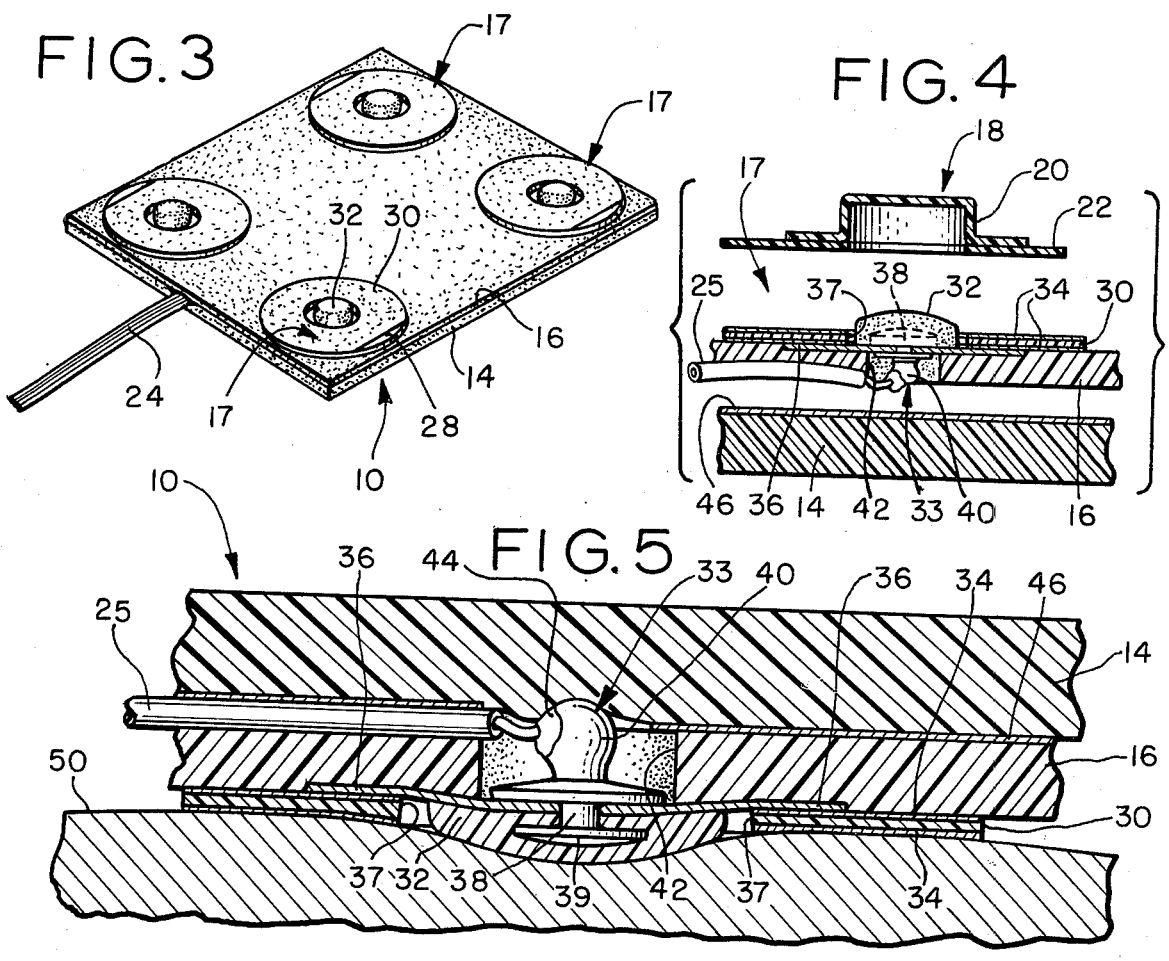

ECG MONITORING PAD

BACKGROUND OF THE INVENTION

The present invention relates to an assembly of an ECG monitoring device including medical electrodes of a known, and accepted design used to detect bio-skin potential, and more particularly said invention to such a monitoring device designed to be easily and economically constructed. This arrangement is particularly useful in operating room and recover room patient ECG monitoring applications.

A number of arrangements for disposable medical electrodes per se for patient ECG monitoring are known in the prior art, as are automated methods of assembly, a general form being shown in U.S. Pat. No. 3,805,769, which is incorporated herein by reference. Typically such medical electrodes comprise a metal conductive member fixed to a foamed plastic or microporous base sheet. In use these sheets are applied to the skin with the aid of a pressure sensitive adhesive surrounding the conductor member, the resilience or flexibility of the sheet cooperating with the adhesive to hold the electrode firmly against the skin. The electrode conductive element is commonly positioned away from the skin to minimize motion artifacts or noise by including a pre-gelled pad overlying the conductive element. The pad and base section are covered by a protective member to be removed prior to use. In addition to the above-noted design for the individual electrode members, there has been developed in the art various types of composite monitoring devices, known as "back pads". These devices normally include a base or substrate with a number of monitoring electrodes mounted thereon. To the best of Applicant's knowledge, these designs employ electrode assemblies that must be meticulously assembled to the base substrate, as they are not capable of manufacture by automated production methods, such as the general type disclosed in said U.S. Pat. No. 3,805,769. As an additional matter, the designs in existence prior to the present invention were not pre-gelled, to the best of Applicant's knowledge.

Briefly, an ECG monitoring device constructed in accordance with the present invention comprises a first or bottom resilient foam or sponge-like sheet and a second or top resilient foam or sponge-like sheet adhesively attached thereto to provide a base substrate to which a plurality of electrode packages are affixed. The top or upper sheet includes a plurality of openings formed therethrough to receive the terminal portions of the medical electrodes for attachment of lead wires thereto.

Each electrode package includes an electrode structure and a cover means, said electrode comprises an adhesively coated base layer, with a terminal or conductive connector assembly engaged on opposite sides thereof, preferably in the form of a snap fastener. A pre-gelled pad is engaged over the connection assembly on the adhesively coated side of the base layer. The cover structure which is removable overlies both said adhesively coated surface and said pad to protect and preserve the integerity of the adhesive and gel electrolyte. The electrode packages are mounted to the base substrate in overlying relation to said openings by a second adhesive layer applied to the opposite side thereof. In this assembled position, a portion of the terminal or connector assembly of each electrode extends from the side of the base layers opposite of said pad, and is aligned with one of said openings. A plurality of lead wires are provided and connected, one to each said conductive terminal assembly. Said lead wires are disposed intermediate the respective sheets and extend from an edge of the device. Preferably, the distal ends of said wires are assembled to a conventional, plug-in type of connector assembly for connecting the device to monitoring apparatus.

With the present invention, it is possible to provide an ECG device of the general type discussed above wherein the individual electrode members are of a known and accepted design, an extremely important factor in light of the passage into law of medical device legislation. Further, these electrode structures are embodied in pre-gelled electrode packages which are manufactured to finish a construction by automated production methods, as alluded to previously. Accordingly, all that need be done is to mount the electrodes to a substrate and connect the lead wires thereto. As can be appreciated, the present design materially reduces the cost of the final product.

Other objects and advantages of the present invention will become apparent from the following detailed description when taken together with the accompanying drawings wherein like numerals are used throughout to designate similar parts and components.

BRIEF DESCRIPTION OF THE DRAWINGS

FIG. 1 is a perspective view of a packaged ECG monitoring device in accordance with the present invention.

FIG. 2 is a fragmentary perspective view of a corner portion of the device of FIG. 1, showing additional details of the construction of said device.

FIG. 3 is a perspective view of the patient engaging surface of an ECG monitoring pad according to the present invention, with the cover means for each electrode removed, preparatory to attachment to a patient.

FIG. 4 is an exploded partial sectional view of one of the monitoring locations on a device according to the present invention.

FIG. 5 is a partial sectional view of a monitoring location on an ECG monitoring device applied to a patient.

DETAILED DESCRIPTION OF THE ILLUSTRATED EMBODIMENT

Referring to FIG. 1, an ECG monitoring device 10 is shown as supplied to a user wrapped in protective packaging material 12. As can be seen the lead wires are attached and the device is ready for connection to monitoring apparatus (not shown).

The monitoring device 10 as shown in the drawings includes a first resilient sponge-like sheet 14 forming a bottom portion thereof and a second resilient sponge-like sheet 16 attached to sheet 14 to provide a top layer, the respective sheets serving to provide a base or substrate 15 upon which a number of medical electrode package assemblies 17 are mounted. The construction of said electrode package assemblies 17 will be described in detail hereinafter.

Sheets 14 and 16 are preferably formed from a relatively resilient foam or sponge-like material such as polyester or polyether material. The medical electrode packages 17 and their associated parts are shown in FIG. 1 mounted to the top or upper sheet 16 and include a removable protective cover assembly 18. Each said cover assembly 18 is composed of an annular disc 22 and upwardly projecting cap or cup member 20 attached to the disc 22. These cover assemblies 18 serve to protect various parts of the electrodes 17 as will be explained in detail later.

As can also be seen, in FIG. 1, a cable or harness made up of a plurality of lead wires 25 forms an integral part of the device 10. There is provided one wire for each electrode 17, with the cable 24 terminating in a suitable plug type connector 26 for attachment of the device 10 to an external ECG readout device. It can be seen in FIG. 1 and the foregoing description thereof that the ECG monitoring device 10 is designed so as to be packaged in a suitable protective material such as a clear plastic or cellophane bag and is relatively flat and compact to permit ease and convenience in the storage and handling thereof prior to use. The packaging material 12 and protective cover members 18 also serve to prevent drying out of the electrode gel and also to keep the ECG monitoring device 10 and its medical electrodes and associated parts relatively clean, dry and sterile prior to the actual use thereof.

Before discussing the construction and preparation of the device 10 for use, it is believed advisable to consider the construction of a prefered electrode package 17, which provides the monitoring stations on device 10, as illustrated in FIGS. 4 and 5. The electrode package 17 as shown in FIG. 4 includes a cover assembly 18 shown in exploded or removed position. This assembly, as alluded to previously comprises an annular disc 22 and a raised cap portion 20 attached to said disc 22. When assembled, cover 18 will overlie the remaining electrode structure to provide a removable protective covering. The remainder of electrode package 17 in effect provides the actual electrode structure that defines the monitoring station, and this structure is shown in FIG. 4, affixed to the top or upper sheet 16. Said remainder portion or electrode structure comprises essentially a base section 30 having an adhesive coating 34 thereon, a gel pad 32 mounted to the base section 30 with a terminal assembly 33 engaged through the base section 30 and in contact with the gel pad 32. This base section 30 may include an aperture 37, as shown, or may be formed as a circular disc. When apertured as at 37, a separate disc member 36 is applied over said aperture 37 and forms an integral part of the base section 30. This disc is attached to the base section 30 by an adhesive surface, which is exposed to the opposite side of said base section through said aperture 37. The gel pad 32 is attached to said exposed adhesive surface of the disc 36, or the adhesive surface 34 of base section 30, if said base section is not apertured. The gel pad 32 overlies a conductive connector or terminal assembly 33, and has a measured quantity of electrolyte gel applied thereto. One of the lead wires 25, which serve to make up cable 24 is soldered or otherwise connected to the conductor assembly 33.

The conductive connector assembly 33 in the illustrated version of the invention is in the form of a conventional snap fastener. More specifically, said assembly 33 is comprised of an inner or eyelet member 38 and an outer cap or stud member 40. As is illustrated in FIGS. 4 and 5, the cap 40 is hollow and has a portion of the eyelet 38 engaged therein. This assembly is achieved by cold forming during the automated manufacture of the electrode member 17, by conventional snap fastener application apparatus. It should be noted, that the eyelet 38 is engaged through the disc 36, and has a substantially flat, flanged portion 39 covered by the gel pad 32.

Attention is now directed to the process for assembling the electrode device 10. It must be kept in mind that the electrode packages 17 are pre-assembled by automated manufacturing apparatus as discussed previously, and are thus complete. That is to say, the complete electrode package 17 including the cover 18, pre-gelled pad 32 and connector 33 are all assembled or mounted to the base section 30. The first step is to then mount the electrodes to the upper or top sheet 16. This is accomplished by use of an adhesive applied to the normally, non-adhesive surfaces of the base section 30 and disc 36. Assembly of the electrode package 17 is effected, such that the stud or cap element 40 of each is disposed within the aperture 42 formed in said sheet 16. Next, the respective lead wires 25 are connected to the stud element 40 by a solder connection 44, or some other permanent or releasable connection means, such as by a female type snap fastener element mounted on the end of wire 25 and engaged over stud 40.

The lower sheet 14, as can be seen in FIG. 4, includes an adhesive coating 46. Accordingly, once the wires 25 are connected, the sheet 14 is engaged with the surface of sheet 16 opposite that to which the electrodes 17 are mounted. The adhesive layer 46 will firmly bond the lower sheet 14 to the sheet 16 and serve to grip the lead wires 25 and maintain them in place. Thus, even if the cable 24 is pulled, the stress produced is not applied to the solder connection due to the firm engagement of said lead wires 25 by the sheets 14 and 16. This serves to reduce the chances that the solder connection 44 will be broken during use.

The procedure for preparing the ECG monitoring device 10 for use, and a number of structural features, thereof, are illustrated in FIGS. 2 and 3. With reference specifically to FIG. 2, it can be seen that the protective cover members 18 for each electrode may be removed immediately prior to use by grasping a flat edge 19 formed at one side thereof and pulling cover member 18 up thus releasing it and the cap 20 from the adhesive coated surface on base section 30 therebelow. It will be noted that a relatively small portion of paper material 28 remains covering a small edge of adhesive disc 30 which may be grasped between a thumb and finger, for example, to aid in the removal of cover member 18 without disturbing adhesive-coated base section 30. Annular disc portion 22 of cover member 18 is made of a suitable release liner type material such as plastic or wax-coated paper to releaseably adhere to adhesive-coated disc 30.

The removal of protective cover members 18 exposes adhesive coated portions on each of the electrodes 17 for contact with the skin of the patient whose ECG or bio-skin potential is to be monitored. In addition, removal of the cover 18 also exposes the pre-gelled pad 32. Each gel-pad 32 as mentioned previously, is soaked with an electrolyte gel or paste material to promote electrical contact between the skin and the electrode conductor assembly 33 disposed immediately thereunder. As an additional feature the cover 18 protects the electrolyte gel or paste material on the gel pad 32 against evaporation and against inadvertant release thereof by application of pressure upon gel pad 32 prior to use thereof.

FIG. 3 shows the ECG monitoring pad 10 removed from packaging material 12 with the protective covers 18 removed and cable 24 extended thus readying monitoring pad 10 for application to a patient.

Referring now to FIG. 5, an enlarged cutaway view of a portion of an ECG monitoring pad 10 is shown in contact with the skin 50 of a patient. The annular disc or base section 30 has its top adhesive coated surface 34 applied directly to the skin, thereby holding the rest of the monitoring pad 10 in position, and holding gel pads 32 directly against the skin 50 to make suitable electrical contact therewith. The electrolyte gel or paste with which gel pad 32 is soaked serves to establish electrical contact between the skin 50 and the conductive connector assembly 33, without direct physical contact of flange 39 with the patient's skin 50. Lead wire 25 runs between sheets 14 and 16 to join with similar wires from the other electrodes of the pad 10 to form cable 24. The opposite ends of said wires, as mentioned previously are joined to a plug-in-type of connector 26 for attachment to a monitoring device.

As can be clearly seen in FIG. 5, the ECG monitoring pad is particularly suited to be used by placing it under the back of a reclining patient so that the electrodes 17 make contact with the skin 50. The sheets 16 and 14 provide suitable padding to prevent any discomfort to the reclining patient which might otherwise be caused by the snap fasteners 38 and 40 or wire 25.

It will be appreciated from the foregoing description and drawings that the ECG monitoring device 10 constructed in accordance with the present invention can be easily and economically manufactured. Further, these devices 10 are relatively comfortable when placed under the back of the reclining patient for monitoring bioskin potential. The ECG monitoring pad made according to the present invention can also be used, of course, in other fashions than under the back of a reclining patient, without departing from the present invention.

The drawing and the foregoing descriptions are not intended to represent the only forms of the invention. The substitution of equivalents is contemplated as circumstances may suggest or render expedient; and although specific terms have been employed, they are intended in a generic and descriptive sense only, and not for the purposes of limitation, the scope of the invention being delineated by the claims appended hereto.

The invention is claimed as follows:

1. An ECG monitoring device comprising: a first resilient sponge-like sheet, a second resilient sponge-like sheet adhesively attached to said first sheet layered relation and having a plurality of openings formed therethrough, and a plurality of electrode assemblies mounted to said second sheet in overlying relation to each of said openings, each said electrode assembly comprising: a base section having an adhesively coated surface on one side thereof, conductive terminal means carried by said base section and including a portion thereof corresponding to each side of said base section, a pre-gelled, sponge-like pad overlying a first portion of said terminal means on the adhesively coated side of said base section, a second portion of said terminal means on the opposite side of said base section being disposed in an associated opening in said second sheet, removable cover means forming part of each said electrode assembly overlying said adhesive surface on said base section and said pre-gelled pad; and a lead wire connected to each of said second terminal portions and extending between said sheets to the exterior thereof.

2. An ECG monitoring device according to claim 1, wherein said base section is apertured and includes a disc member overlying said aperture, with said terminal means engaged through said disc member.

3. An ECG device according to claim 2, wherein said disc member includes an adhesive surface attaching same to said base section, a portion of said adhesive surface of said disc member being exposed through said aperture, and said sponge-like pad being secured to said adhesive surface of said disc member.

4. ECG monitor of claim 2 wherein said removable cover means comprises a generally flat annular release liner removably attached to the adhesive surface of said base section, and a generally circular raised cup portion attached to said liner and disposed generally above said gel-pad.

5. An ECG monitoring device according to claim 1, wherein said terminal means comprises a conductive snap fastener having a female member and a male member, said male member and female member engaging one another through said base section.

6. The ECG monitoring pad of claim 1 wherein said first and second sheets are generally rectangular and congruent and said plurality of openings comprises four openings disposed in said second sheet so as to define substantially the corners of a rectangle thereon congruent with said rectangular shape of said second sheet.

7. An ECG monitoring device comprising: a substrate; a plurality of pre-assembled electrode packages mounted to said substrate, each said pre-assembled electrode package, including a base section having a first, adhesive surface, terminal means carried by said base section, a pre-gelled pad carried by said base section in overlying contact with said terminal means, and cover means overlying said adhesive surface and said pre-gelled pad; said substrate including, a first layer and a second layer having a plurality of apertures formed therein, adhesive means securing a pre-assembled electrode package to said substrate in overlying relation to each aperture formed therein with said pre-gelled pad projecting therefrom, a plurality of lead wires disposed intermediate said first and second layers, with one said lead wire connected to each of said electrode terminal means through each said aperture and extending to the exterior to said substrate, and adhesive means joining said first layer to said second layer to fix said lead wires in position.

8. A device according to claim 7 wherein said first and second layers are provided by resilient sponge-like sheets.

9. A device according to claim 7, wherein said cover means includes a disc formed of a release liner material and removably engaged with a portion of said adhesive surface on said base section, and a raised cap member engaged on said disc to overlie said pre-gelled pad.

10. A device according to claim 7, wherein said base section is comprised of an annular member defining a central aperture, and a disc member engaged over said aperture.

11. A method of assembling an ECG device of the type including a substrate with a plurality of monitoring stations thereon, said method comprising the steps of, providing a first sheet of material having two or more apertures therein; providing a number of electrode packages corresponding to said apertures, each said electrode package provided being completely assembled and having an adhesive coated base section, terminal means carried thereby, a pre-gelled pad carried by said base section in association with said terminal means, and a protective cover structure removably secured to said base section and overlying said gel pad; securing an electrode package to a first surface of said first sheet in overlying relation to each said aperture, with the terminal means of each package disposed proximate said aperture and said cover structure disposed outwardly of said first surface, attaching a lead wire to each said terminal means from the opposite surface of said first sheet, and attaching a second sheet of material to the said opposite surface of said first sheet in overlying relation to said lead wires and terminal means, with said first and second sheets providing said substrate.

12. A method according to claim 11, wherein said step of providing said electrode packages includes the step of mass producing said electrode packages in complete, assembled form.

13. A method according to claim 11 wherein the step of securing the electrode package to the first sheet, includes the step of applying an adhesive to the normally non-adhesive surface of said package, opposite that defined by said cover means.

* * * * *